United States Patent
Miyamoto

(10) Patent No.: US 8,611,988 B2
(45) Date of Patent: Dec. 17, 2013

(54) PROJECTION IMAGE GENERATION APPARATUS AND METHOD, AND COMPUTER READABLE RECORDING MEDIUM ON WHICH IS RECORDED PROGRAM FOR THE SAME

(75) Inventor: Masaki Miyamoto, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 160 days.

(21) Appl. No.: 13/016,131

(22) Filed: Jan. 28, 2011

(65) Prior Publication Data

US 2011/0245660 A1   Oct. 6, 2011

(30) Foreign Application Priority Data

Mar. 31, 2010 (JP) .................................. 2010-084272

(51) Int. Cl.
 *A61B 5/05* (2006.01)
(52) U.S. Cl.
 USPC ............ 600/427; 600/424; 600/425; 600/426
(58) Field of Classification Search
 USPC ................................................. 600/424–427
 See application file for complete search history.

(56) References Cited

U.S. PATENT DOCUMENTS

| | | | | |
|---|---|---|---|---|
| 5,638,819 A | * | 6/1997 | Manwaring et al. | 600/424 |
| 7,536,216 B2 | * | 5/2009 | Geiger et al. | 600/407 |
| 2002/0128547 A1 | | 9/2002 | Furuhashi et al. | |
| 2005/0033117 A1 | * | 2/2005 | Ozaki et al. | 600/109 |
| 2005/0113643 A1 | * | 5/2005 | Hale et al. | 600/118 |
| 2005/0215854 A1 | * | 9/2005 | Ozaki et al. | 600/109 |
| 2006/0002626 A1 | * | 1/2006 | Matsumoto | 382/276 |
| 2006/0149147 A1 | * | 7/2006 | Yanof | 600/424 |
| 2007/0154075 A1 | * | 7/2007 | Matsumoto | 382/128 |
| 2008/0247619 A1 | | 10/2008 | Li | |
| 2009/0156895 A1 | * | 6/2009 | Higgins et al. | 600/104 |

FOREIGN PATENT DOCUMENTS

| | | |
|---|---|---|
| JP | 2003-339644 | 12/2003 |
| JP | 2005-021353 | 1/2005 |
| JP | 2007-007041 | 1/2007 |
| JP | 2009-211138 | 9/2009 |

OTHER PUBLICATIONS

Japanese Official Action—2010-084272—Jul. 16, 2013.

* cited by examiner

*Primary Examiner* — Unsu Jung
*Assistant Examiner* — Rajeev Siripurapu
(74) *Attorney, Agent, or Firm* — Young & Thompson

(57) ABSTRACT

When generating a projection image which is an image formed of image information on a plurality of visual lines viewing a first structure in a three-dimensional medical image from a given viewpoint being projected on a given projection plane, setting an assumed position of a treatment tool in the three-dimensional image, detecting a surface of the first structure from the three-dimensional medical image, identifying a second structure in the three-dimensional medical image located at a position masked by the first structure, detecting an intersection point between an assumed path formed when the treatment tool is moved from the assumed position towards the second structure and the surface of the first structure, and displaying the intersection point in an identifiable manner at a position to which image information on a visual line connecting the viewpoint and the intersection point is projected.

20 Claims, 10 Drawing Sheets

PROJECTION IMAGE GENERATION APPARATUS AND METHOD, AND COMPUTER READABLE RECORDING MEDIUM ON WHICH IS RECORDED PROGRAM FOR THE SAME

BACKGROUND OF THE INVENTION

1. Field of the Invention

The present invention relates to a technology for generating a projection image which is an image formed of image information on a plurality of visual lines viewing a structure in a three-dimensional medical image from a predetermined viewpoint being projected on a predetermined projection plane.

2. Description of the Related Art

Recently, with the advancement of modalities, such as multidetector-row CT (MDCT), high quality three-dimensional image data have become available. In image diagnosis using such image data, virtual or pseudo three-dimensional subject images have been used more frequently, as well as high resolution cross-sectional images. Further, the extraction of organ structures from three-dimensional medical images using image recognition technologies are also performed, and it has become possible to generate virtual or pseudo three-dimensional images from three-dimensional medical images of well distinguished structures. Then, the images so generated are used in the planning and simulations prior to surgery and navigations during surgery.

As for the method of generating a virtual or pseudo three-dimensional image, a method using rendering technology, such as surface rendering or volume rendering is known. In particular, an image obtained by perspective projection (central projection) from a virtual viewpoint inside of a subject is called a virtual endoscopic image, which is an image as if observed by an endoscope.

Technologies for supporting endoscopic surgery using such virtual endoscopic images are proposed.

For example, U.S. Patent Application Publication No. 20020128547 describes an apparatus that detects a position of an endoscope by a sensor and generates, with the detected position as the viewpoint, a virtual endoscopic image having a wider field angle than the endoscope, and displays a real endoscopic image captured by the endoscope and the virtual endoscopic image in a superimposing manner.

Further, Japanese Unexamined Patent Publication No. 2005-021353 describes an apparatus that detects a position of an endoscope in real time, generates a virtual endoscopic image having the same field of view as that of the endoscope and visualizing a vascular arrangement within the field of view, detects a position of a treatment tool used in the endoscopic surgery in real time, generates a composite image by combining an image representing the treatment tool to the virtual endoscopic image at the position of the treatment tool, and displays the composite image and a real endoscope image.

In an endoscopic surgery, the visual line direction differs from the operation direction of the treatment tool. This makes it difficult, even by observing, in perspective, a lesion in an organ using virtual endoscopic images from endoscope viewpoints described in the patent documents described above, to understand the operation direction of the treatment tool, i.e., the state in an approaching path of the treatment tool towards a lesion in the images. For example, for a virtual endoscopic image in which the visual direction VL corresponds to the center of the field of view, as schematically illustrated in FIG. 7, it is difficult to understand a position where the treatment tool enters into an organ. Although it is possible to observe other structures present in the organ, such as a blood vessel and the like, to be taken into account for the surgery by translucent processing, it is difficult to understand whether or not such a structure is present in the path of the treatment tool from the entry position to the lesion.

The present invention has been developed in view of the circumstances described above, and it is an object of the present invention to provide an apparatus and method for generating a projection image that allows easy understanding of the state of an approaching path of a treatment tool for an attention structure masked by another structure, such as a lesion in an organ. It is a further object of the present invention to provide a computer readable recording medium on which is recorded a projection image generation program of the present invention.

SUMMARY OF THE INVENTION

A projection image generation apparatus of the present invention is an apparatus having a projection image generation means for generating, using a three-dimensional medical image as input, a projection image which is an image formed of image information on a plurality of visual lines viewing a first structure in the three-dimensional medical image from a given viewpoint being projected on a given projection plane, the apparatus further including:

a treatment tool position setting means for setting an assumed position of a treatment tool in a coordinate space of the three-dimensional medical image;

a surface detection means for detecting a surface of the first structure from the three-dimensional medical image;

a second structure identification means for identifying a second structure in the three-dimensional medical image located at a position masked by the first structure when the first structure is viewed from the assumed position of the treatment tool; and an intersection point detection means for detecting an intersection point between an assumed path formed when the treatment tool is moved from the assumed position towards the second structure and the surface of the first structure, wherein the projection image generation means is a means that generates a projection image in which the intersection point is displayed in an identifiable manner at a position on the projection plane to which image information on a visual line connecting the viewpoint and the intersection point is projected.

A projection image generation method of the present invention is a method having the step of generating, using a three-dimensional medical image as input, a projection image which is an image formed of image information on a plurality of visual lines viewing a first structure in the three-dimensional medical image from a given viewpoint being projected on a given projection plane, the method further including the steps of:

setting an assumed position of a treatment tool at a position on the front and outside of the first structure when the first structure is viewed from the viewpoint in a coordinate space of the three-dimensional medical image;

detecting a surface of the first structure from the three-dimensional medical image;

identifying a second structure in the three-dimensional medical image located at a position masked by the first structure when the first structure is viewed from the assumed position of the treatment tool; and detecting an intersection point between an assumed path formed when the treatment tool is moved from the assumed position towards the second structure and the surface of the first structure, wherein the step of generating a projection image is a step that generates a projection image in which the intersection point is displayed in an identifiable manner at a position on the projection plane to which image information on a visual line connecting the viewpoint and the intersection point is projected.

A computer readable recording medium on which is recorded a projection image generation program of the present invention is a medium on which is recorded a program for causing a computer to perform the function of each means of the projection image generation apparatus described above as a processing step, thereby causing the computer to function as the projection image generation apparatus.

Here, the "first structure" is a structure that masks the "second structure" when the first structure is viewed from the assumed position of the treatment tool. A specific example of the "first structure" and the "second structure" may be the case in which a lesion, which is the second structure, is present inside of an organ, which is the first structure. Otherwise, it may be the case in which the second structure is behind the first structure when the first structure is viewed from the assumed position of the treatment tool. Another specific example of the "first structure" may be a body surface. On the other hand, the "second structure" is typically a treatment target by a treatment tool, i.e., a target region for surgery.

The projection method from the given viewpoint to the given projection plane for generating the "projection image" may be a central project or a parallel projection on the assumption that the viewpoint is at infinity.

When "image information on a plurality of visual lines" is projected, image information on each visual line may be image information obtained by interpolation using image information of adjacent pixels to the visual line.

The "given viewpoint" may be a position manually set by the user or a position in the three-dimensional coordinate space of the three-dimensional medical image corresponding to a position of an endoscope inserted into a body cavity of a subject detected in real time by an endoscope position detection means.

In this case, an arrangement may be adopted in which a real endoscopic image representing an inside of the body cavity is formed by real time imaging and a superimposed image in which the real endoscopic image and a projection image based on the position of the endoscope detected by the endoscope position detection means at substantially the same timing as that of the formation of the real endoscopic image are superimposed is generated.

The "assumed position of a treatment tool" may be a position manually set by the user or a position in the three-dimensional coordinate space of the three-dimensional medical image corresponding to a position of a treatment tool inserted into a body cavity of a subject detected in real time by a treatment tool position detection means.

The method of "detecting the first structure" and the method of "detecting the second structure" may be an automatic method using a known image recognition technology, a manual method by user, or a combination thereof.

A specific example of the method of "detecting an intersection point" may be a method that detects the intersection point by projecting the second structure onto a portion of the surface of the first structure located in the direction from the second structure towards the assumed position of the treatment tool. In this case, the intersection point may be displayed in the projection image "in an identifiable manner" by projecting the second structure projected on the portion of the surface of the first structure onto the projection plane from the given viewpoint. Here, it is preferable that the second structure projected on the portion of the surface of the first structure is projected onto the projection plane by a parallel projection.

In this case, a third structure located in front of the second structure when the second structure is viewed from a position of the treatment tool may further be projected onto a portion of the surface of the first structure located in the direction from the second structure towards the assumed position of the treatment tool. A specific example of the "third structure" may be an anatomical structure that requires attention in surgery, such as a blood vessel, an organ, a tumor, or the like.

According to the present invention, when generating, using a three-dimensional medical image which includes a second structure masked by a first structure when the first structure is viewed from an assumed position of a treatment tool as input, a projection image which is an image formed of image information on a plurality of visual lines from a given viewpoint being projected on a given projection plane, an intersection point between an assumed path formed when the treatment tool is moved from the assumed position towards the second structure and the surface of the first structure is detected, and the intersection point is displayed in an identifiable manner at a position on the projection plane of the projection image to which image information on a visual line connecting the viewpoint and the intersection point is projected. This allows the entry position of the treatment tool into the first structure masking the second structure, i.e., an attention target, to be understood in the projection image from the given viewpoint. If the projection image from the given viewpoint is used as an image from a viewpoint used in ordinary diagnosis, surgery simulation, or surgery navigation, the observer may understand the state of the approaching path of the treatment tool to an attention structure (second structure) masked by another structure (first structure), like a lesion in an organ, with the same feeling as that when observing an affected area in ordinary surgery without having uncomfortable feeling or confusion, which contributes to the improvement of the accuracy and safety of surgery.

DESCRIPTION OF THE PREFERRED EMBODIMENTS

Figure 1:
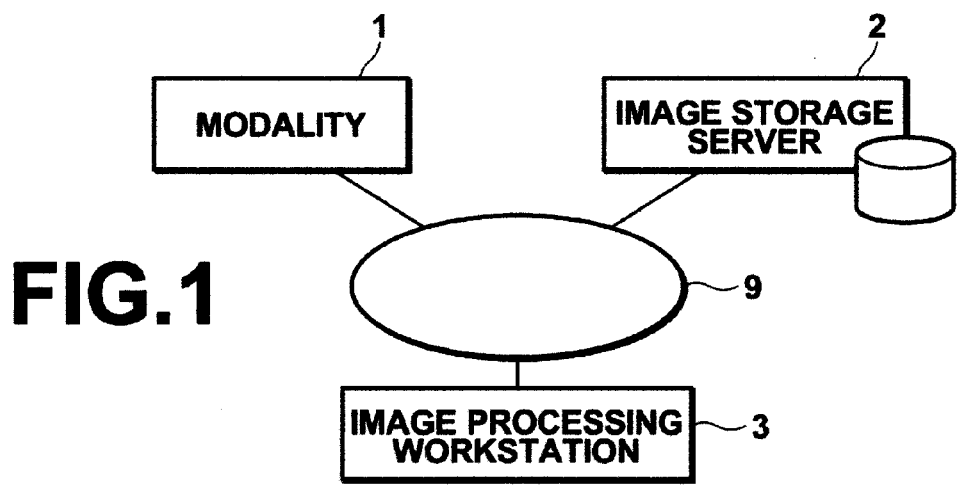
FIG. 1 is a schematic configuration diagram of a medical image diagnosis system in which a surgery simulation function according to an embodiment of the present invention is implemented.

FIG. 1 is a schematic hardware configuration diagram of a medical image diagnosis system in which a surgery simulation function is implemented according to a first embodiment of the present invention. As shown in FIG. 1, the system includes modality 1, image storage server 2, and image processing workstation 3 communicatably connected to each other via network 9.

Modality 1 includes an apparatus that images an inspection target region of a subject to generate image data representing a three-dimensional medical image of the region and outputs the image data by attaching auxiliary information defined in DICOM (Digital Imaging and Communication in Medicine) standard as image information. Specific examples of the apparatus include, for example, CT, MRI, and the like. In the present embodiment, a description will be made of a case in which three-dimensional image data representing an abdominal region of a human body, including liver, to be examined are generated by scanning the human body with CT in a body axis direction.

Image storage server 2 is a computer for storing medical image data, in a database, obtained by modality 1 and image data of a medical image generated by image processing in image processing workstation 3 and managing them, and includes a large capacity external memory unit and database management software (e.g., Object Relational Database (ORDB)).

Image processing workstation 3 is a computer that performs image processing (including image analysis) on medical image data obtained from modality 1 or image storage server 2 and displays a generated image in response to a request from a radiology reader. It is provided with a known hardware configuration of a CPU, a main storage unit, an auxiliary storage unit, an input/output interface, a communication interface, input devices (mouse, keyboard, and the like), a display device (display monitor), a data bus, and the like, and has a known operating system installed thereon. The surgery simulation function using the projection image generation process of the present invention is implemented in the image processing workstation 3 and the process is realized by executing a program installed from a recording medium, such as a CD-ROM or the like. Alternatively, the program may be a program installed after being downloaded from a storage unit of a server connected via a network, such as Internet or the like.

The storage format of image data and communication between each component of the system via network 9 are based on the DICOM protocol or the like.

Figure 2:
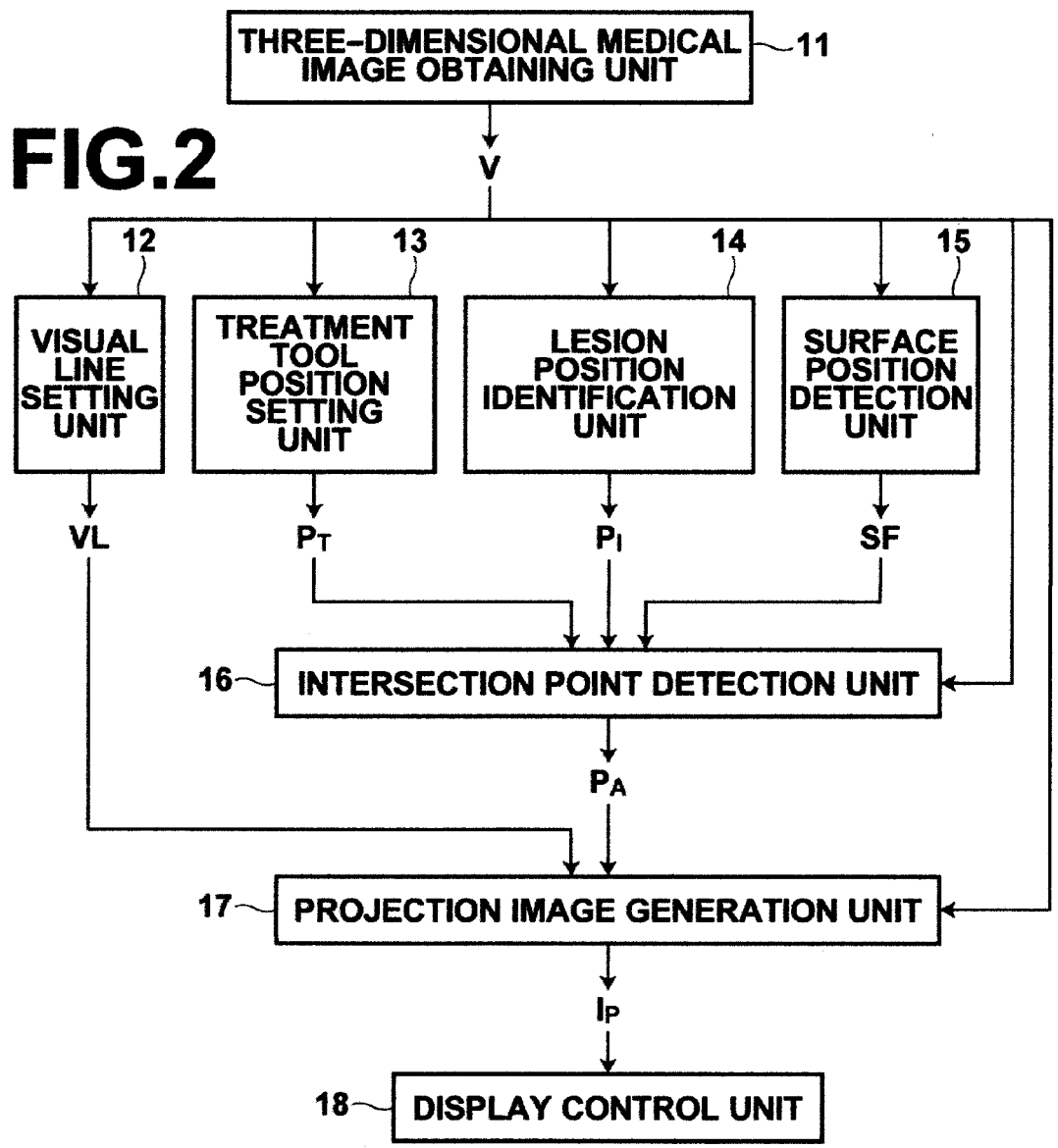
FIG. 2 is a block diagram schematically illustrating a configuration and a process flow for realizing the surgery simulation function in the first embodiment of the present invention.

FIG. 2 is a block diagram illustrating a portion of the function of image processing workstation 3 relevant to the surgery simulation process according to a first embodiment of the present invention. As shown in FIG. 2, the surgery simulation process according to the first embodiment of the present invention is realized by three-dimensional image obtaining unit 11, visual line setting unit 12, treatment tool position setting unit 13, lesion position identification unit 14, surface position detection unit 15, intersection point detection unit 16, projection image generation unit 17, and display control unit 18. In FIG. 2, three-dimensional medical image V, projection image $I_P$, visual line VL in projection image $I_P$, treatment tool assumed position (hereinafter, treatment tool position) $P_T$, liver lesion position $P_I$, liver surface position SF, and intersection point $P_A$ between a treatment tool operation direction and a liver surface position are data written into and read out from a predetermined memory area of image processing workstation 3 by each of the units described above.

Figure 3:
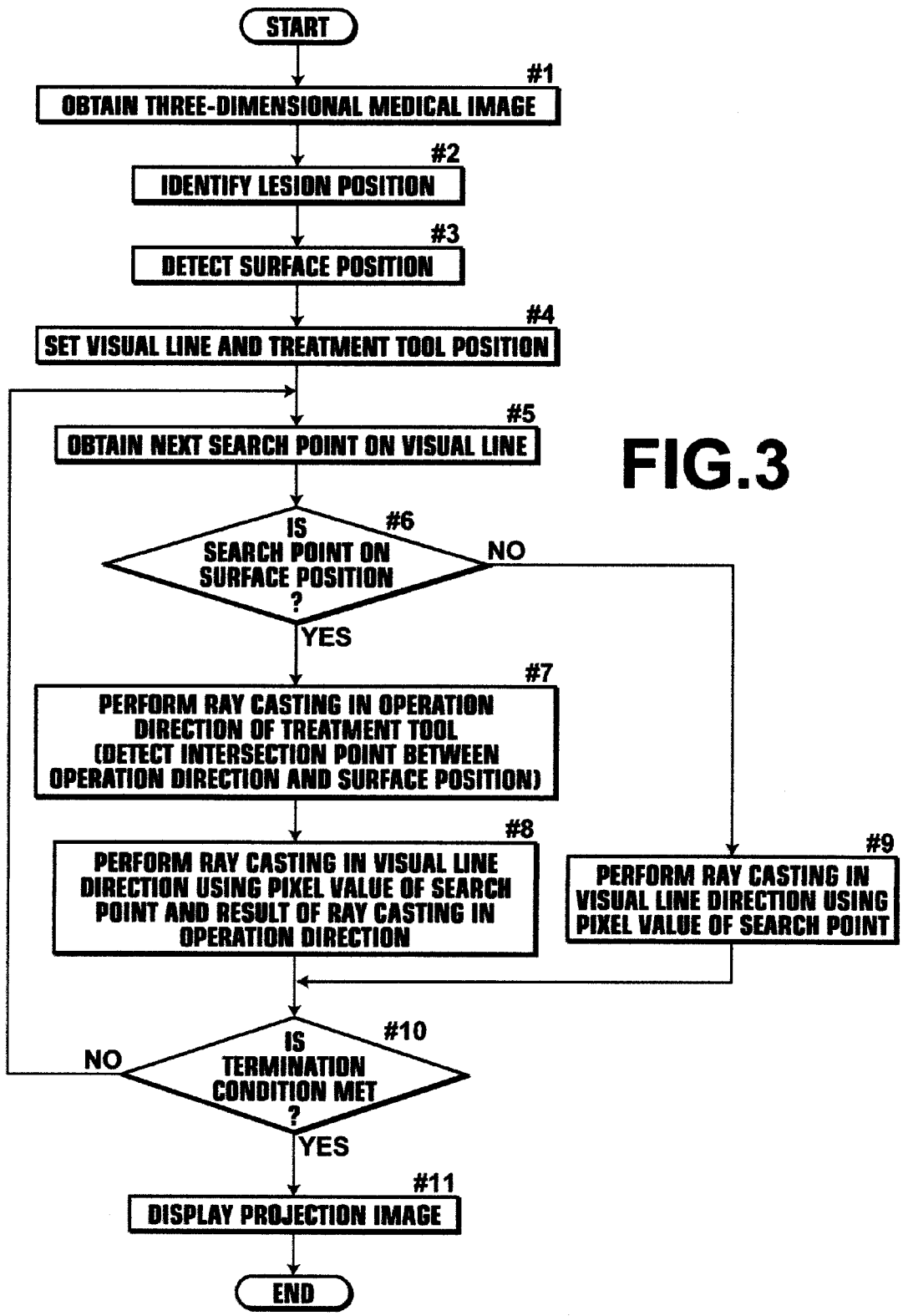
FIG. 3 is a flowchart illustrating a process flow of surgery simulation using a medical image diagnosis system according to an embodiment of the present invention.

FIG. 3 is a flowchart illustrating a flow of user operation, calculation processing, display processing, and the like performed under the execution of software for the surgery simulation according to the first embodiment of the present invention. A flow of surgery simulation of the first embodiment of the present invention will be described with reference to FIGS. 2 and 3.

First, an abdominal region of a subject is imaged by modality 1 and a three-dimensional image V is formed. In image processing workstation 3, three-dimensional image obtaining unit 11 obtains the three-dimensional image V formed by modality 1 (#1), lesion position identification unit 14 extracts a lesion in the liver represented by the three-dimensional medical image V and identifies the position $P_I$ thereof (#2), and surface position detection unit 15 detects a surface position SF of the liver (#3). In the mean time, visual line setting unit 12 and treatment tool position setting unit 13 set a visual line VL of a projection image $I_P$ to be generated in a subsequent step and a position $P_T$ of a treatment tool used for surgery respectively based on a user operation (#4).

Then, using the three-dimensional image as input, projection image generation unit 17 generates a projection image $I_P$ which is an image generated by projecting image information on a plurality of visual lines set by visual line setting unit 12 onto a predetermined projection plane (#5, #6, #8, #9, #10). At that time, intersection point detection unit 16 detects an intersection point $P_A$ between an assumed path (operation direction) to be formed when the treatment tool is moved from the treatment tool position set by the treatment tool position setting unit 13 towards the lesion position $P_I$ identified by lesion position identification unit 14 (#7), and projection image generation unit 17 generates a projection image $I_P$ in which the intersection point $P_A$ detected by intersection point detection unit 16 is displayed in an identifiable manner at the position to which image information on the visual line VL passing through the intersection point $P_A$ is projected (#8). Although the series of processing will be described in detail later, intersection point detection unit 16 in the present embodiment is adapted to detect the intersection point $P_A$ by parallel projecting the lesion position $P_I$ extracted by lesion position identification unit 14 to a surface SF of the liver in an operation direction of the treatment tool and the processing of intersection point detection unit 16 is performed serially in the projection processing of the projection image generation unit 17 with respect to each visual line.

Thereafter, display control unit 18 causes the generated projection image $I_P$ to be displayed on the display device of image processing workstation 3 (#11).

Processing performed in each unit of image processing workstation 3 will now be described in detail.

Three-dimensional medical image obtaining unit 11 has a communication interface function to receive a three-dimensional medical image V from modality 1 and to store the image V in a predetermined memory area of image processing workstation 3.

Figure 4:
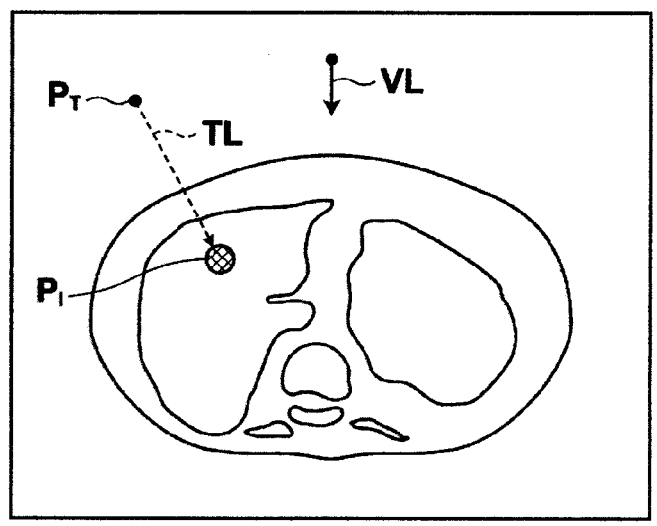
FIG. 4 schematically illustrates an example screen for setting a visual line and a position of a treatment tool.

Visual line setting unit 12 and treatment tool position setting unit 13 provide a user interface, including a setting screen shown in FIG. 4 as an example, to respectively accept a user operation for setting a visual line VL in a projection image $I_P$ and a position $P_T$ of a treatment tool used for surgery. As illustrated in FIG. 4, visual line setting unit 12 and treatment tool position setting unit 13 generate an axial cross-sectional image based on the three-dimensional medical image V and causes the generated image to be displayed in the setting screen. Here, the position of the axial cross-sectional image may be, for example, a position passing through the center of lesion position $P_I$ identified by lesion position identification unit 14 prior to the generation of the axial cross-sectional image. Further, the position of the cross-section may be changed according to a user operation using a keyboard, a pointing device, or the like. A marker is superimposed on an area representing the lesion (area indicated by $P_I$ in the drawing). For example, if an icon for setting a visual line is selected by the user from a tool bar (not shown) using a pointing device and then an arrow (VL in the drawing) indicating a visual line direction is depicted by performing a drag operation while keeping a click operation at a desired position in the axial cross-sectional image, visual line setting unit 12 detects the operation and determines the direction of the visual line VL in a coordinate space of the three-dimensional medical image V and stores the determination result in a predetermined memory space. In the mean time, for example, if an icon for setting a position of the treatment tool is selected by the user from a tool bar (not shown) using a pointing device and then a click operation is performed at a desired assumed position (point $P_T$ in the drawing) of the treatment tool in the axial cross-sectional image, treatment tool position setting unit 13 detects the operation and identifies the position of the treatment tool position $P_T$ in the coordinate space of the three-dimensional medical image V and stores the identification result in a predetermined memory space. Note that the direction of the treatment tool toward the center of lesion position $P_I$, i.e., the operation direction of the treatment tool (TL in the drawing) is determined by the determination of the treatment tool position $P_T$.

Lesion position identification unit 14 uses a three-dimensional medical image V as input and extracts a surgery target liver lesion area from the image V using a known image recognition method, thereby identifying a lesion position $P_I$. For example, when the method proposed by the present applicant in U.S. Patent Application Publication No. 20080247619 is used, lesion position identification unit 14 may extract a lesion area by accepting user setting of an arbitrary point in a lesion area in an axial cross-sectional image through a pointing device operation or the like, determining a three-dimensional possible existing range of the lesion area using information of possible size of the lesion area defined in advance, and using a region splitting method, such as graph cuts based on the point set by the user and a point outside of the existing range. In the present embodiment, the lesion position $P_I$ refers to a mass of points representing a three-dimensional lesion area extracted by lesion position identification unit 14. Hereinafter, the lesion position $P_I$ may sometimes be called as the lesion area $P_I$ according to the context.

Surface position detection unit 15 uses a three-dimensional medical image V as input and detects a surface position SF of a liver from the image V using a known image recognition method. For example, when the method proposed by the present applicant in Japanese Unexamined Patent Publication No. 2009-211138 is used, a liver region is detected from the three-dimensional medical image by surface position detection unit 15 in the following manner. First, in response to a user operation of a pointing device or the like in an axial cross-sectional image representing a liver, an arbitrary point in the liver region is set by the user (hereinafter, user set point). Then an angulated portion of a contour of the liver region is detected as a reference point using a discriminator obtained through machine learning, such as AdaBoost method. Then, with respect to each point (voxel) in a three-dimensional area (hereinafter, processing target area) of a size sufficient to include the liver region centered on the user set point, an evaluation value that indicates whether or not each point is a point on the contour of the liver region is calculated using the discriminator obtained through machine learning, such as AdaBoost method. Then, after each point on a circumference of the processing target area is determined as a point in a background area outside of the liver area while the user set point and the reference point are determined as point in the liver area, and the liver area is extracted from the three-dimensional medical image V by applying a graph-cut method using the evaluation value of each point in the processing target area. Here, the contour of the extracted liver area is the surface position SF.

Intersection point detection unit 16 applies a known ray casting method to project the lesion position $P_I$ onto the surface position SF in the operation direction TL of the treatment tool, thereby obtaining an intersection point $P_A$ between the operation direction TL of the treatment tool and surface position SF of the liver, i.e., the entry position of the treatment tool into the liver.

In the mean time, projection image generation unit 17 generates a projection image $I_P$ using the three-dimensional medical image V as input and performing parallel projection onto the direction of visual line VL using a volume rendering method that employs known ray casting.

In the present embodiment, intersection point detection unit 16 and projection image generation unit 17 perform the processing integrally as shown in steps #6 to #10 of the flowchart in FIG. 3. Hereinafter, the processing will be described with reference to the schematic diagram illustrated in FIG. 5. Not that it is predefined by a program startup parameter or by a setting file that color information (each signal value of R, G, B) $C_I$ and opacity $\alpha_I (=1)$ is allocated to each voxel belonging to the lesion position $P_I$ identified by lesion position identification unit 14, color information $C_{SF}$ and opacity $\alpha_{SF} (=1)$ are allocated to each voxel representing the surface position SF of the liver detected by surface position detection unit 15, and color information $C_{OT}$ and opacity $\alpha_{OH} (=0)$ are allocated to the other area.

First, projection image generation unit 17 reads information of the first search point on a visual line VL (#5) and determines whether or not the search point is on the surface position SF (#6). More specifically, a determination is made as to whether or not the search point itself or at least one of adjacent eight voxels is on the surface position SF. If the search point is not on the surface position SF (#6: NO), ray casting (visual line direction ray casting) is performed using the color information and opacity allocated to the search point (#9). On the other hand, if the search point is on the surface position SF (#6: YES), intersection point detection unit 16 performs ray casting from the search point toward inside of the subject in an operation direction TL (operation direction ray casting) to obtain calculation results of color information $C_{TL}$ and cumulative opacity $\alpha_{TL}$ (#7). Then, based on the color information $C_{SF}$ allocated to the search point on the surface position SF, and the color information $C_{TL}$ and cumulative opacity $\alpha_{TL}$ obtained by the operation direction ray casting, projection image generation unit 17 replaces the color information of the search point with $\alpha_{TL} \cdot C_{TL} + (1-\alpha_{TL}) \cdot C_{SF}$ and performs visual line direction ray casting (#8). This terminates ray casting with respect to one search point in the visual line direction. At this point of time, if a termination condition of the visual line direction ray casting is met, i.e., if the cumulative opacity $\alpha_{VL}$ reaches a value of 1 in the visual line direction ray casting or if the search point is outside of the range of the three-dimensional medical image V (#10: YES), the visual line direction ray casting is terminated. On the other hand, if the termination condition is not met (#10: NO), information of the next search point in the visual line direction is obtained (#5), and steps #6 to #9 are repeated until the termination condition is met (#10: YES). Although it is not clearly indicated in the flowchart of FIG. 3, steps #5 to #10 are performed with respect to each of a plurality of visual lines corresponding to each pixel constituting the projection image $I_P$ in parallel or series.

Figure 5:
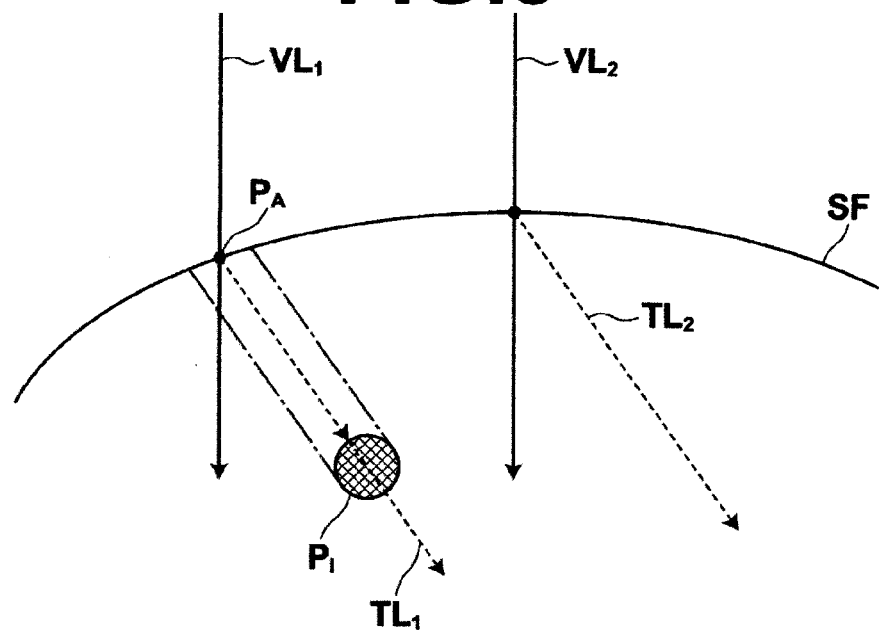
FIG. 5 schematically illustrates ray casting in a visual line direction and ray casting in an operation direction of a treatment tool.

In the example shown in FIG. 5, the opacity $\alpha_{OH}$ of each search point in the visual line direction ray casting along each of visual lines $VL_1$ and $VL_2$ is a value of 0 until the search point reaches the surface position SF of the liver and, therefore, color information is not accumulated. When the search point reaches the surface position SF of the liver in each visual line direction ray casting, ray casting along the operation direction $TL_1$ and ray casting along the operation direction $TL_2$ are performed. With respect to the search point on the visual line $VL_1$ which is on the surface position SF of the liver, the opacity $\alpha_{OH}$ of each search point is a value of 0 in the operation direction ray casting from the search point until the search point reaches the lesion area $P_I$ and, therefore, the color information $C_{TL1}$ and cumulative opacity $\alpha_{TL1}$ are not accumulated. When the search point reaches the lesion area $P_I$, however, the color information $C_I$ is accumulated and, as the opacity $\alpha_I$ of each search point in the lesion area $P_I$ is a value of 1, a termination condition of the operation direction ray casting (same as the termination condition of the visual line direction) is met, whereby the operation direction ray casting is terminated. Therefore, the color information $C_{TL1}$ (=color information $C_I$ in the lesion area $P_I$) and cumulative opacity $\alpha_{TL1}$ (=opacity $\alpha_I$ in the lesion area $P_I$=1) are obtained by the operation direction ray casting. Here, referring back to the visual line direction ray casting, from the color information $C_{SF}$ allocated to the surface position SF of the liver, color information $C_{TL1}$ (=$C_I$) and cumulative opacity $\alpha_{TL1}$ (=1) obtained by the operation direction ray casting, the color information of the search point is $\alpha_{TL1} \cdot C_{TL1} + (1-\alpha_{TL1}) \cdot C_{SF} = C_I$, and the opacity $\alpha_{SF}$ allocated to the search point on the surface position SF of the liver is a value of 1, whereby the termination condition of the visual line direction ray casting is also met and the ray casting is terminated. This results in that the color information of the pixel of the projection image $I_P$ corresponding to the visual line $VL_1$ is $C_I$. In the mean time, with respect to the search point on the visual line $VL_2$ which is on the surface position SF of the liver, the opacity $\alpha_{OH}$ of each of all search points in the operation direction $TL_2$ is a value of 0 since no search point in the lesion area $P_I$ is present in the direction, so that the search point reaches outside of the range of the three-dimensional medical image V without the color information $C_{TL2}$ and cumulative opacity $\alpha_{TL2}$ being accumulated, whereby the termination condition is met and the operation direction ray casting is terminated with each of the color information $C_{TL2}$ and cumulative opacity $\alpha_{TL2}$ remaining at a value of 0. Here, referring back to the visual line direction ray casting, from the color information $C_{TL2}$ (=0) and cumulative opacity $\alpha_{TL2}$ (=0) obtained by the operation direction ray casting, the color information of the search point is $\alpha_{TL2} \cdot C_{TL2} (1-\alpha_{TL2}) \cdot C_{SF} = C_{SF}$, and the opacity $\alpha_{SF}$ allocated to the search point on the surface position SF of the liver is a value of 1, whereby the termination condition of the visual line direction ray casting is also met and the ray casting is terminated. This results in that the color information of the pixel of the projection image $I_P$ corresponding to the visual line $VL_2$ is $C_{SF}$.

As described above, the combined performance of the visual line direction ray casting and operation direction ray casting causes the lesion area $P_I$ to be parallel projected on the surface SF of the liver in the operation direction and color information different from that of the other area of the surface of the liver to be projected on the projection plane of the projection image $I_P$ by the parallel projection in the visual line direction. That is, the intersection point $P_A$ between the operation path of the treatment tool from the treatment tool position $P_T$ towards the lesion position $P_I$ and the surface SF of the liver is detected and displayed in the projection image $I_P$ in an identifiable manner.

Figure 6:
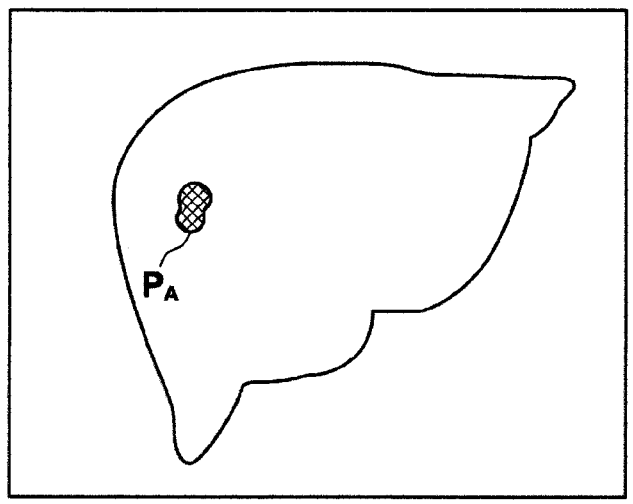
FIG. 6 schematically illustrates an example of a projection image generated in the first embodiment of the present invention.
Figure 7:
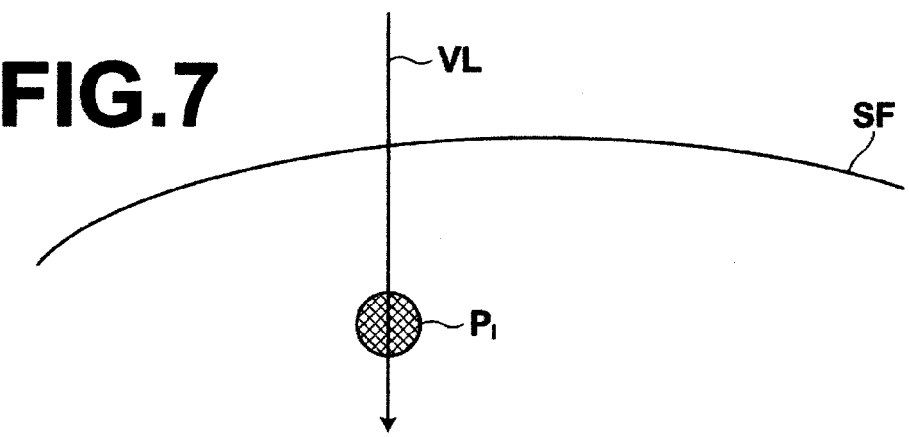
FIG. 7 schematically illustrates ray casting in a visual line direction in a comparative example of the present invention.
Figure 8:
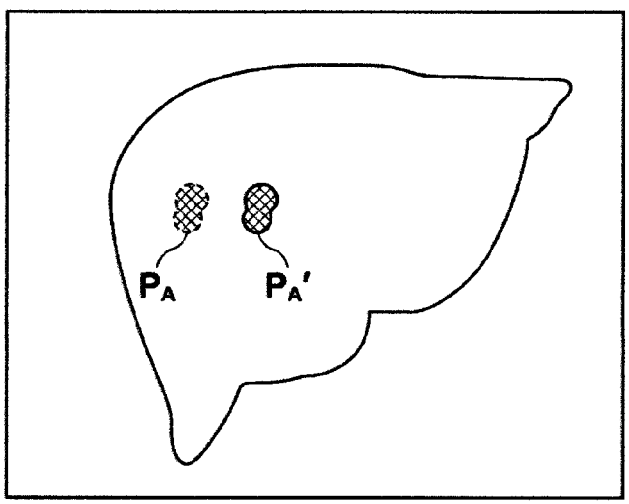
FIG. 8 schematically illustrates an example of a projection image generated in the comparative example of the present invention.

FIG. 6 schematically illustrate an example of the projection image $I_P$ generated in the manner as described above. As illustrated in FIG. 6, an intersection point $P_A$, which is an entry position of a treatment tool moved from an assumed position $P_T$ toward a lesion area $P_I$, is superimposed on a volume rendering image in which a surface SF of a liver is projected In contrast, FIGS. 7 and 8 illustrate a comparative example of the first embodiment of the present invention. As schematically illustrated in FIG. 7, when a lesion area $P_I$ is parallel projected on a surface position SF of a liver along a visual line VL, the generated projection image becomes like that shown in FIG. 8, and the projection position $P_A'$ of the lesion area $P_I$ is different from the projection position $P_A$ in the first embodiment of the present invention, resulting in that the projection position $P_A'$ does not correspond to the entry position of the treatment tool. Note that the projection position $P_A$ in FIG. 8 is illustrated for comparison purposes only and is not actually depicted by the projection method shown in FIG. 7.

As described above, according to the first embodiment of the present invention, when a projection image $I_P$, which is an image formed of image information on a plurality of visual lines VL set by visual line setting unit 12 being projected on a predetermined projection plane, is generated by projection image generation unit 17 using a three-dimensional medical image V as input, a lesion area $P_I$ identified by lesion position identification unit 14 is parallel projected on a surface of a liver in an operation direction of a treatment tool, which is a direction of the treatment tool when the treatment tool is moved from an assumed position $P_T$ thereof set by treatment tool position setting unit 13 to the lesion area $P_I$, by intersection point detection unit 16 to detect an intersection point $P_A$, and a projection image $I_P$ in which the detected intersection point $P_A$ is displayed in an identifiable manner at the position to which image information on the visual line passing through the detected intersection point $P_A$ is projected can be generated by projection image generation unit 17. This allows the entry position of the treatment tool into the liver having the lesion area $P_I$ to be understood easily and appropriately in the projection image $I_P$. Further, the projection image $I_P$ may have a field of view identical to that of surgery. Therefore, the use of the projection image $I_P$ in surgery simulation allows the observer to understand the state of the approaching path of the treatment tool to the lesion area $P_I$ in the liver with the same feeling as that when observing an affected area in ordinary surgery without having uncomfortable feeling or confusion, which contributes to the improvement of the accuracy and safety of surgery.

Further, the lesion position $P_I$ extracted by lesion position identification unit 14 is parallel projected on the surface SF of the liver along the operation direction of the treatment tool, the shape and size of the lesion position $P_I$ are directly reflected, whereby a projection image $I_P$ more appropriate for the observation can be obtained.

In the embodiment described above, intersection point detection unit 16 and projection image generation unit 17 perform the processing integrally. But an arrangement may be adopted in which intersection point detection unit 16 projects the lesion area $P_I$ onto the surface SF of the liver along the operation direction TL and replaces the color information of the position on the surface SF of the liver to which the lesion area $P_I$ is projected with $\alpha_{TL} \cdot C_{TL} + (1-\alpha_{TL}) \cdot C_{SF}$, then projection image generation unit 17 performs parallel projection in the visual line direction VL. Alternatively, an arrangement may be adopted in which projection image generation unit 17 performs parallel projection in the visual line direction VL first, then intersection point detection unit 16 projects the lesion area $P_I$ onto the surface SF of the liver along the operation direction TL, then identifies a position in the projection image $I_P$ to which the projected position $P_A$ is projected, and replaces the color information of the identified position with $\alpha_{TL} \cdot C_{TL} + (1-\alpha_{TL}) \cdot C_{SF}$.

A second embodiment of the present invention is an embodiment in which color information $C_X (\ne 0)$ and opacity $\alpha_X (0 < \alpha_X < 1)$ are allocated to a structure $P_X$ inside of a liver, such as a blood vessel, and the opacity $\alpha_I$ of the lesion area $P_I$ is changed in the range of $0 < \alpha_I < 1$. Further, intersection point detection unit 16 and projection image generation unit 17 do not perform the processing integrally, and the processing is performed in the order of intersection point detection unit 16 and projection image generation unit 17 or in the reverse order, as described above.

Figure 9:
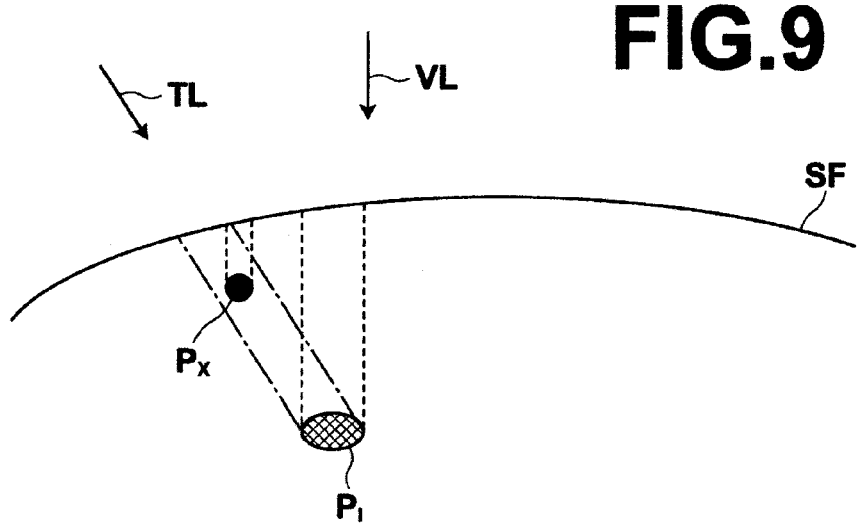
FIG. 9 schematically illustrates ray casting in a second embodiment of the present invention and ray casting in a comparative example of the second embodiment.
Figure 10:
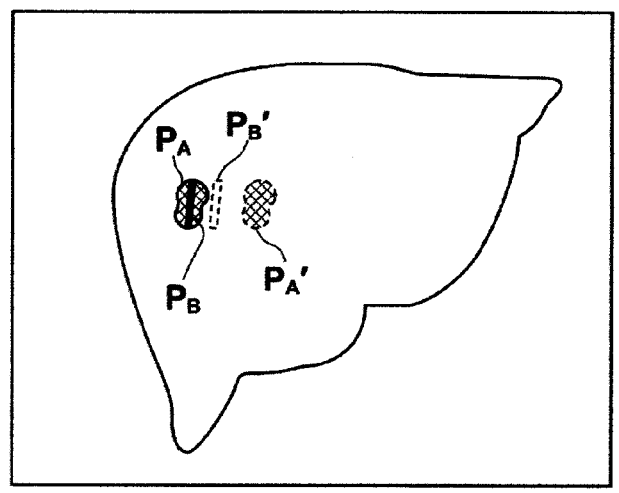
FIG. 10 schematically illustrates an example of projection images generated in the second embodiment of the present invention and the comparative example of the second embodiment.

This causes a structure $P_X$ which has the color information $C_X$ and opacity $\alpha_X$ allocated thereto and lies on the straight line connecting between the treatment tool position $P_T$ and lesion area $P_I$, as well as the lesion area $P_I$, is projected on the surface SF of the liver when the ray casting is performed by intersection point detection unit 16 in the operation direction TL of the treatment tool, as schematically illustrated in FIG. 9. FIG. 10 schematically illustrates a projection image $I_P$ generated in the second embodiment of the present invention. As illustrated in FIG. 10, an area $P_A$ representing the lesion area $P_I$ and an area $P_B$ representing the other structure $P_X$ are projected on the position where the operation direction TL intersects with the surface SF of the liver in the projection image $I_P$. This allows the positional relationship between the lesion area $P_I$ and the other structure $P_X$ in the operation direction TL of the treatment tool to be understood easily and a structure to be careful at the time of surgery ($P_X$ in this example) can be discovered easily, whereby the accuracy and safety of surgery may be further improved. In the mean time, as in the comparative example of the first embodiment of the present invention, when the lesion area $P_I$ and the other structure $P_X$ are projected in the visual line direction VL, they are projected like $P_A'$ and $P_B'$ respectively in the projected image $I_P$, whereby it is difficult to understand the positional relationship between the lesion area $P_I$ and the other structure $P_X$ in the operation direction TL of the treatment tool.

Figure 11:
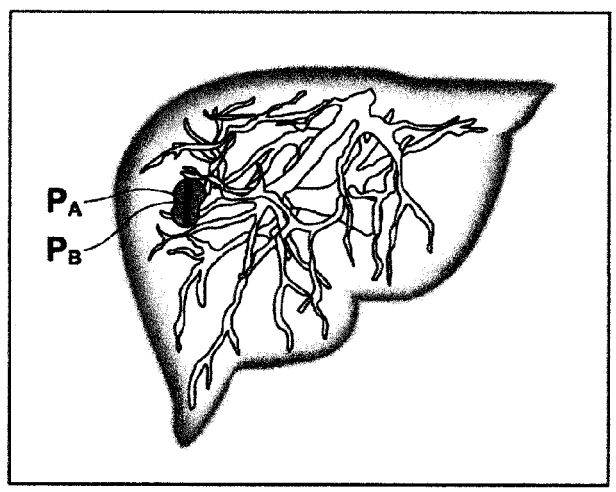
FIG. 11 schematically illustrates an example of a projection image generated in a third embodiment of the present invention.

A third embodiment of the present invention is identical to the second embodiment except that the opacity $\alpha_{SF}$ allocated to the surface SF of the liver is changed in the range of $0 < \alpha_{SF} < 1$. As schematically illustrated in FIG. 11, this allows a projection image $I_P$, which is a volume rendering image in which the surface SF of the liver is made translucent and a structure inside of the liver, such as a blood vessel and the like, is made visually recognizable with the lesion area $P_I$ and the structure $P_X$ being projected on the surface SF of the liver in the operation direction TL of the treatment tool and superimposed, to be generated, thereby facilitating the observation of the internal structure of the liver while allowing the understanding of the entry position of the treatment tool.

Figure 12:
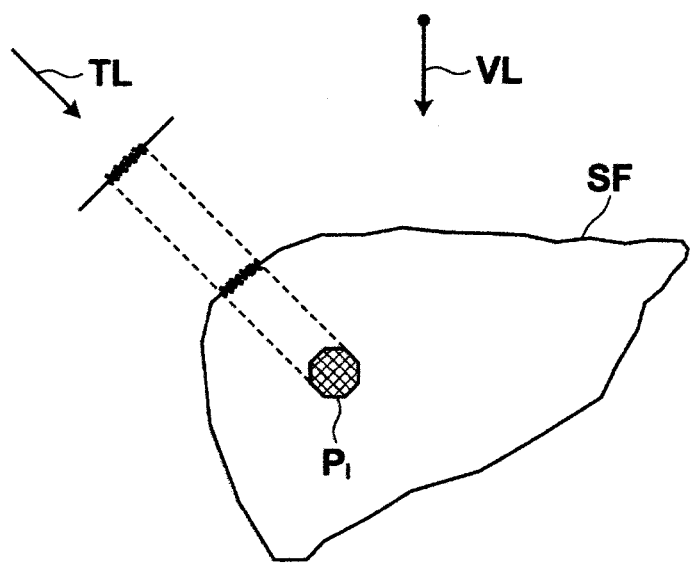
FIG. 12 schematically illustrates an aspect of how a projection image is generated by surface rendering in a fourth embodiment of the present invention.

A fourth embodiment of the present invention is an embodiment in which a projection image $I_P$ is generated using a known surface rendering method. More specifically, as schematically illustrated in FIG. 12, lesion position identification unit 14 generates a surface model $P_I$ of a lesion area and surface position detection unit 15 generates a surface model SF of a liver, intersection point detection unit 16 attaches a texture representing the surface model $P_I$ of the lesion area at the intersection between the surface model $P_I$ when it is projected in the operation direction TL of the treatment tool and the surface model SF of the liver, and projection image generation unit 17 generates a projection image $I_P$ in which the surface model SF of the liver to which the texture representing the surface model $P_I$ of the lesion area is attached is visualized. This may provide advantageous effects identical to those of the first embodiment, although the rendering method is different.

Figure 13:
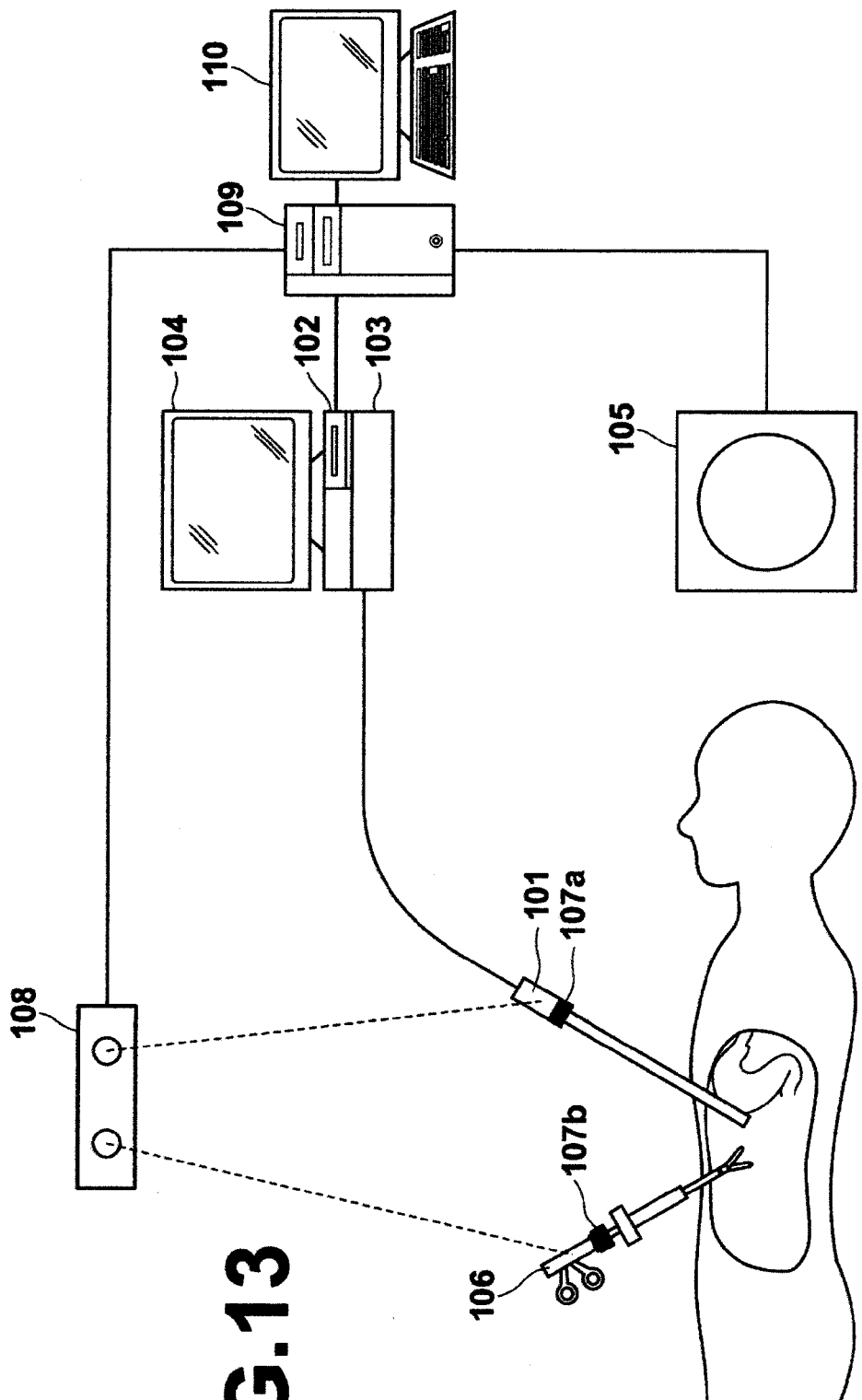
FIG. 13 illustrates a hardware configuration of an endoscopic examination support system in which a surgery navigation function is implemented according to a fifth embodiment of the present invention.

A fifth embodiment of the present invention is an endoscopic examination support system in which a surgery navigation function is implemented. FIG. 13 is a hardware configuration diagram of the endoscopic examination support system, illustrating an overview thereof. As shown in FIG. 13, the system includes endoscope 101, digital processor 102, light source unit 103, real endoscopic image display 104, modality 105, treatment tool 106, endoscope marker 107*a*, treatment tool marker 107*b*, position sensor 108, image processing workstation 109, and display 110 for the image processing workstation (hereinafter, WS display).

In the present embodiment, endoscope 101 is a rigid endoscope for abdominal cavities and inserted into an abdominal cavity of a subject. The light guided through an optical fiber from light source unit 103 is outputted from a tip portion of endoscope 101 and an image of the inside of the abdominal cavity of the subject is obtained by an imaging optical system of endoscope 101. Digital processor 102 converts the image signal obtained by endoscope 101 to a digital image signal, corrects image quality by performing digital signal processing such as white balance adjustment, shading correction, and the like, and outputs the corrected image signal as real endoscopic image data ($I_{RE}$) by attaching auxiliary information defined by DICOM standard. The outputted real endoscopic image data ($I_{RE}$) are transmitted to image processing workstation 109 via a LAN according to a communication protocol conforming to the DICOM standard. Further, digital processor 102 converts the real endoscopic image data ($I_{RE}$) to an analog signal and outputs the analog signal to real endoscopic image display 104, whereby a real endoscopic image ($I_{RE}$) is displayed on real endoscopic image display 104. Image signals are obtained by endoscope 101 at a predetermined frame rate and real endoscopic image display 104 displays the real endoscopic image ($I_{RE}$) as a motion picture representing the inside of the abdominal cavity. Further, endoscope 101 may also obtain a still image according to a user operation.

Modality 105 is identical to modality 1 in the first to fourth embodiments, and formed three-dimensional image data (V) are transmitted to image processing workstation 109 via the LAN according to the communication protocol conforming to the DICOM standard.

Endoscope marker 107a, treatment tool marker 107b, and position sensor 108 constitute a known three-dimensional position measuring device. Endoscope marker 107a and treatment tool marker 107b are provided near the grip of endoscope 101 and treatment tool 106 respectively, and a three-dimensional position of each of markers 107a and 107b is detected by optical position sensor 108 at a predetermined time interval. Each of endoscope marker 107a and treatment tool marker 107b includes a plurality of marker pieces, and position sensor 108 may detect the orientation of endoscope 101 and treatment tool 106 from the positional relationship between each marker piece and may calculate three-dimensional positions ($PS_E$, $PS_T$) of tip portions of endoscope 101 and treatment portion 106 by offset calculation. Position sensor 108 transmits the calculated three-dimensional position data ($PS_E$, $PS_T$) of endoscope 101 and treatment tool 106 to image processing workstation 109 via a USB interface.

Image processing workstation 109 is a computer provided with a known hardware configuration of a CPU, a main storage unit, an auxiliary storage unit, an I/O interface, a communication interface, a data bus, and the like, and input devices (pointing device, keyboard, and the like) and WS display 110 are connected thereto. Image processing workstation 109 is connected to digital processor 102 and modality 105 through a LAN connection and to position sensor 108 through a USB connection. Further, image processing workstation 109 has a known operating system and various types of application software installed thereon. The application for executing the surgery navigation of the present invention is also installed. These software may be installed from a recording medium, such a as a CD-ROM or the like or installed after being downloaded from a storage unit of a server connected via a network, such as Internet or the like.

Figure 14:
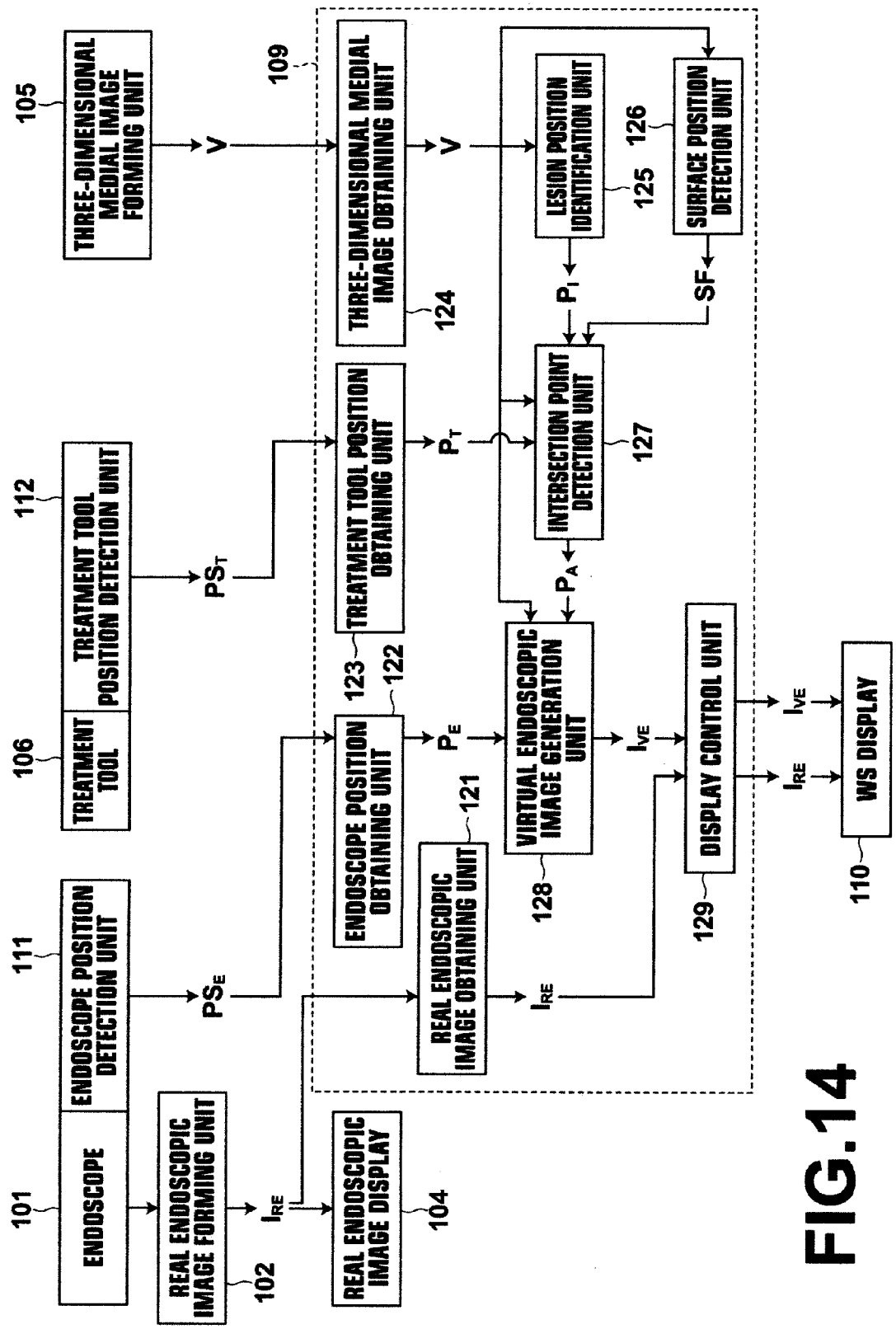
FIG. 14 is a functional block diagram of the endoscopic examination support system of the fifth embodiment.

FIG. 14 is a block diagram, divided based on the function, of an endoscopic examination support system according to a fifth embodiment of the present invention. As illustrated in FIG. 14, the endoscopic examination support system according to the fifth embodiment of the present invention includes endoscope 101, real endoscopic image forming unit 102, real endoscopic image display 104, three-dimensional image forming unit 105, treatment tool 106, WS display 110, endoscope position detection unit 111, treatment tool position detection unit 112, real endoscopic image obtaining unit 121, endoscope position obtaining unit 122, treatment tool position obtaining unit 123, three-dimensional image obtaining unit 124, lesion position identification unit 125, surface position detection unit 126, intersection point detection unit 127, virtual endoscopic image generation unit 128, and display control unit 129. Note that the same reference numerals are used for hardware devices shown in FIG. 13 and functional blocks shown in FIG. 14 which are substantially in one-to-one correspondence. That is, the function of real endoscopic image forming unit 102 is realized by the digital processor shown in FIG. 13 and the function of three-dimensional image forming unit 105 is realized by the modality shown in FIG. 13. In the mean time, the function of endoscope position detection unit 111 is realized by endoscope marker 107a and position sensor 108, and the function of treatment tool position detection unit 112 is realized by treatment tool marker 107b and position sensor 108. The dashed box in FIG. 14 indicates image processing workstation 109, and the function of each unit in the dashed box is realized by executing a predetermined program on the image processing workstation 109. Further, the real endoscopic image $I_{RE}$, endoscope position $P_E$, treatment tool position $P_T$, three-dimensional medical image V, lesion position $P_I$, surface position SF of a structure masking a lesion (hereinafter, masking structure), virtual endoscopic image $I_{VE}$ shown in the dashed box are data written into and read out from a predetermined memory area of image processing workstation 109 by each of the units in the dashed box.

A flow of user operations performed in the endoscopic examination support system according to the fifth embodiment of the present invention and processing performed in each unit described above will now be described roughly using the flowchart shown in FIG. 15.

First, prior to an interior examination of an abdominal cavity of a subject using endoscope 101, a three-dimensional medical image V is formed by imaging the inside of the abdominal cavity of the subject with three-dimensional image forming unit 105. In image processing workstation 109, three-dimensional image obtaining unit 124 obtains the three-dimensional medical image V (#101), and lesion position identification unit 125 extracts a lesion area appearing in the three-dimensional medical image V and identifies the position $P_T$ (hereinafter, also referred to as lesion area $P_T$, as in the first embodiment) (#102), and surface position detection unit 126 detects a surface position SF of a masking structure from the three-dimensional medical image V (#103).

Figure 15:
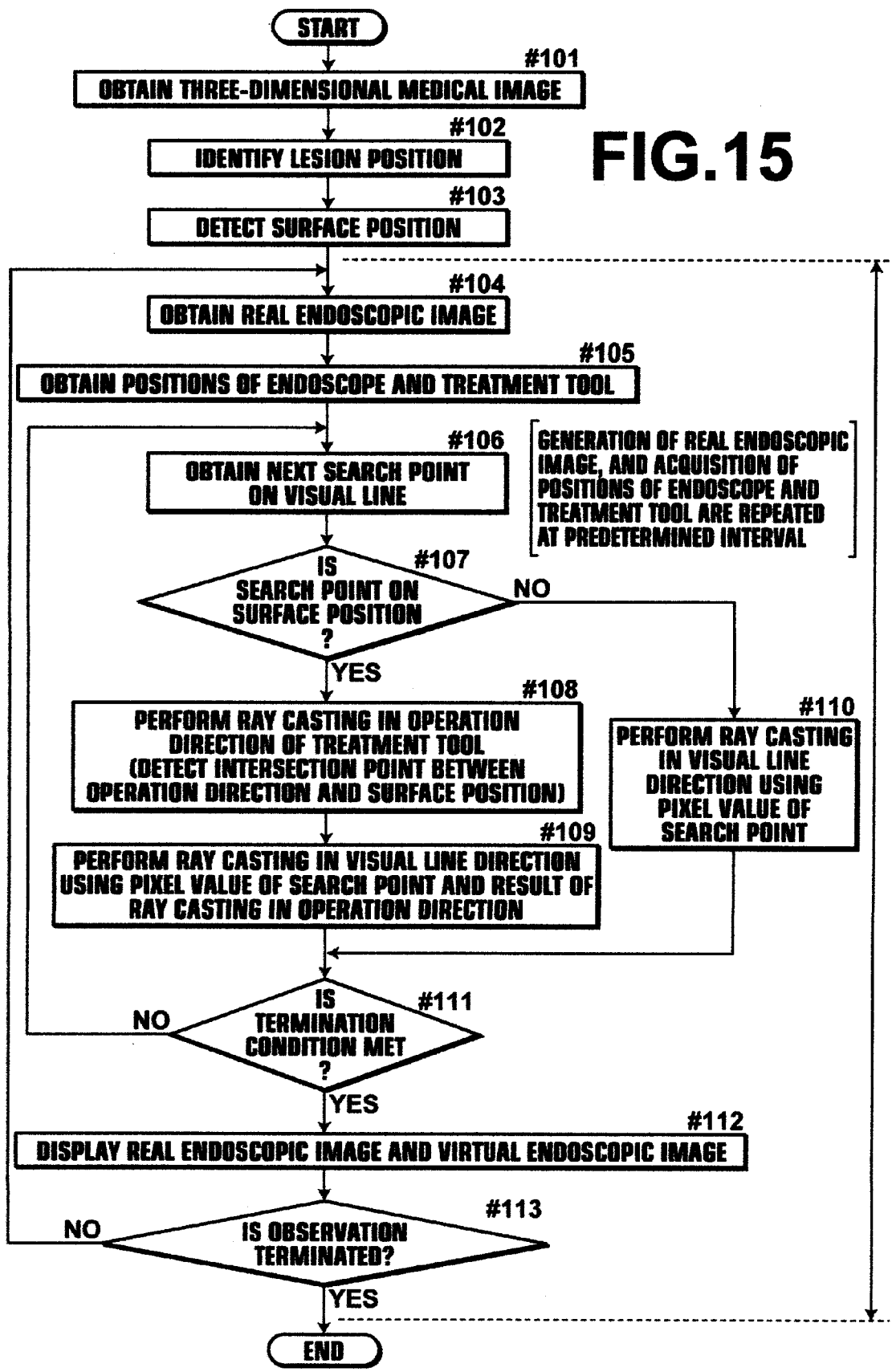
FIG. 15 is a flowchart illustrating a process flow of surgery navigation using the endoscopic examination support system of the fifth embodiment.

As described on the right of the flowchart in FIG. 15, real endoscopic image forming unit 102 repeatedly forms the real endoscopic image $I_{RE}$ by endoscope 101 inserted into the body cavity at a predetermined frame rate and the formed real endoscopic image $I_{RE}$ is displayed on real endoscopic image display 104 in real time as a through motion picture during an endoscopic surgery of the lesion area $P_T$, i.e., during observation of the inside of the abdominal cavity of the subject, until the observation is completed (#113: YES). Endoscope position detection unit 111 and treatment tool position detection unit 112 repeatedly detect, in real time, the positions $PS_E$ and $PS_T$ of endoscope 101 and treatment tool 106 inserted into the body cavity respectively at a predetermined time interval.

In image processing workstation 109, real endoscopic image obtaining unit 121 obtains the real endoscopic image $I_{RE}$ formed by real endoscopic image forming unit 102 (#104). At substantially the same timing, endoscope position obtaining unit 122 obtains the endoscope position $PS_E$ detected by endoscope position detection unit 111, converts the obtained endoscope position $PS_E$ to a position in a coordinate system of the three-dimensional medical image V, and outputs the obtained endoscope position $P_E$, while treatment tool position obtaining unit 123 obtains the treatment tool position $PS_T$ detected by treatment tool position detection unit 112, converts the obtained treatment tool position $PS_T$ to a position in the coordinate system of the three-dimensional medical image V, and outputs the obtained treatment tool position $P_T$ (#105).

Using the three-dimensional medical image V obtained by three-dimensional image obtaining unit 124 as input, virtual endoscopic image generation unit 128 generates a virtual endoscopic image $I_{VE}$, which is an image formed of image information on a plurality of visual lines, with the endoscope position $P_E$ obtained by endoscope position obtaining unit 122 being assumed as the viewpoint, central projected on a predetermined projection plane (#106, #107, #109, #110, #111). At that time, intersection point detection unit 127 detects an intersection point $P_A$ between an assumed path (operation direction) to be formed when the treatment tool is moved from the treatment tool position $P_T$ obtained by treatment tool position obtaining unit 123 towards the lesion position $P_T$ identified by lesion position identification unit 125 and the surface SF of the masking structure detected by surface position detection unit 126 (#108). Then, virtual endoscopic image generation unit 128 generates a virtual endoscopic image $I_{VE}$ in which the intersection point $P_A$ is displayed in an identifiable manner at the position to which image information on the visual line passing through the intersection point $P_A$ detected by intersection point detection unit 127 is projected (#109).

Then, display control unit 129 causes the real endoscopic image $I_{RE}$ obtained by real endoscopic image obtaining unit 121 and virtual endoscopic image $I_{VE}$ generated by virtual endoscopic image generation unit 128 to be displayed in a superimposed manner on WS display 110 (#112).

In image processing workstation 109, acquisition of a new real endoscopic image $I_{RE}$ (#104), acquisition of an endoscope position $P_E$ and a treatment tool position $P_T$ at that time (#105), generation of a virtual endoscopic image $I_{VE}$ (#106 to #111) and update of the superimposed display of the real endoscopic image $I_{RE}$ and virtual endoscopic image $I_{VE}$ (#112) are repeated unless an operation instructing termination of the observation is performed (#113: NO).

Next, processing performed in each unit of image processing workstation 109 will be described in detail.

Real endoscopic image obtaining unit 121 is a communication interface for receiving a real endoscopic image $I_{RE}$ through communication with real endoscopic image forming unit (digital processor) 102 and storing the received image in a predetermined memory area of image processing workstation 109. Based on a request from real endoscopic image obtaining unit 121, a real endoscopic image $I_{RE}$ is transferred from real endoscopic image forming unit 102.

Endoscope position obtaining unit 122 has a function of communication interface for obtaining an endoscope position $PS_E$ through communication with endoscope position detection unit 111 and a function to transform the obtained endoscope position $PS_E$ to an endoscope position $P_E$ represented by coordinate values in a three-dimensional coordinate system of the three-dimensional medical image V from a three-dimension coordinate system of position sensor 108 and to store the endoscope position $P_E$ in a predetermined memory area of image processing workstation 109. In the former communication interface function, an endoscope position $PS_E$ is obtained from endoscope position detection unit 111 based on a request from endoscope position obtaining unit 122. In the latter coordinate transformation function, if the rotation amount of each axis is obtained in advance based on the correspondence relationship between an orientation of each coordinate axis of the three-dimensional coordinate system of the position sensor and an orientation of each coordinate axis of the three-dimensional coordinate system of the three-dimensional medical image V in advance and coordinate values in the three-dimensional coordinate system of position sensor 108 is measured for the position in the subject corresponding to the origin of the three-dimensional medical image V and the translation amount between the two corresponding coordinate axes is obtained in advance based on the coordinate values of the origin in advance, then the endoscope position $PS_E$ represented in the three-dimensional coordinate system of position sensor 108 can be transformed into the endoscope position $P_E$ represented by the coordinate values of the three-dimensional coordinate system of the three-dimensional medical image V using a matrix that performs rotation by the rotation amount and translation by the translation amount.

Treatment tool position obtaining unit 123, like endoscope position obtaining unit 122, has a function of communication interface for obtaining a treatment tool position $PS_T$ through communication with treatment tool position detection unit 112 and a function to transform the obtained treatment tool position $PS_T$ to an endoscope position $P_T$ represented by coordinate values in the three-dimensional coordinate system of the three-dimensional medical image V from the three-dimension coordinate system of position sensor 108 and to store the treatment tool position $P_T$ in a predetermined memory area of image processing workstation 109.

Three-dimensional image obtaining unit 124 has a function of communication interface for receiving a three-dimensional medical image V from three-dimensional medical image forming unit 105 and storing the received image in a predetermined memory area of image processing workstation 109.

Lesion position identification unit 125 is identical to lesion position identification unit 14 of the first to fourth embodiments.

Surface position detection unit 126 detects a surface SF of a masking structure by a method that employs a known image recognition technology, as in the first embodiment, or by detecting a position on each visual line in the central projection from the endoscope position $P_E$ where the pixel value changes rapidly more than a predetermined threshold value or a position where the pixel value becomes greater than a predetermined threshold value.

Intersection point detection unit 127 is identical to intersection point detection unit 16 of the first to fourth embodiments other than that the treatment tool position $P_T$ is the actual position of treatment tool 106 obtained from treatment tool position obtaining unit 123.

Virtual endoscopic image generation unit 128 is identical to projection image generation unit 17 of the first to fourth embodiments other than that a projection image is generated by the central projection with the actual position $P_E$ of endoscope 101 obtained by endoscope position obtaining unit 122 being as the viewpoint instead of the parallel projection in the direction of visual line VL. That is, virtual endoscopic image generation unit 128 corresponds to the projection image generation means.

Thus, steps #106 to #111 in FIG. 15 are identical to steps #5 to #10 in FIG. 3. That is, the combined performance of the visual line direction ray casting by virtual endoscopic image generation unit 128 and operation direction ray casting by intersection point detection unit 127 causes the lesion area $P_I$ to be parallel projected on a surface SF of a masking structure in the actual operation direction of treatment tool 106 and color information different from that of the surface SF of the masking structure to be projected on the projection plane of the virtual endoscopic image $I_{VE}$ by the central projection from the actual endoscope position $P_E$.

Figure 16:
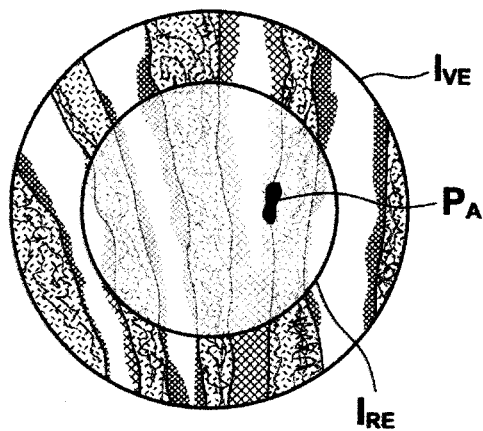
FIG. 16 schematically illustrates an example of a display image in which an actual endoscopic image and a virtual endoscopic image are superimposed on top of each other in the fifth embodiment of the present invention.

Display control unit 129 generates a display image in which the real endoscopic image $I_{RE}$ and virtual endoscopic image $I_{VE}$ are superimposed on top of each other such that the center of field of view corresponds to each other and outputs the display image to WS display 110. For the superimposition of the two images, a known alpha blending process may be used. FIG. 16 schematically illustrates an example of such display image, in which a real endoscopic image $I_{RE}$ and a virtual endoscopic image $I_{VE}$ having a wider field of view are superimposed and a lesion area $P_I$ projected on a surface SF of a masking structure in an operation direction is displayed in the virtual endoscopic image $I_{VE}$ in an identifiable manner as $P_A$.

As described above, in the fifth embodiment of the present invention, intersection point detection unit 127 determines the operation direction into which the lesion position $P_I$ is projected using the actual real time position $P_T$ of treatment tool 106 detected by treatment tool position detection unit 112 and coordinate transformed by treatment tool position obtaining unit 123, and virtual endoscopic image generation unit 128 generates the virtual endoscopic image $I_{VE}$ with the actual real time position $P_E$ of endoscope 101 detected by endoscope position detection unit 111 and coordinate transformed by endoscope position obtaining unit 122 being the viewpoint of the central projection. This allows a so-called augmented reality display to be realized, wherein a virtual endoscopic image $I_{VE}$ in which the field of view of the virtual endoscope and entry position $P_A$ of treatment tool 106 into a masking structure are changed in real time by the feedback of real time detection results of the positions of endoscope 101 and treatment tool 106 by endoscope position detection unit 111 and treatment tool position detection unit 112 is continuously displayed, whereby an endoscopic surgery may be supported dynamically and appropriately.

The embodiments described above are illustration purposes only and many not be construed as limiting the scope of the technical scope of the present invention.

It should be appreciated that various modifications and changes made to the system configurations, hardware configurations, processing flows, module structures, user interfaces, specific processing contents, and the like in the embodiments described above without departing from the spirit of the present invention are included in the scope of the present invention.

For example, with respect to the system configurations, a plurality of image processing workstations 3 may be provided in the system configuration in FIG. 1 and the processing may be shared by each workstation. Further, in the system configuration in FIG. 13, an image storage server may be connected to the LAN, and a three-dimensional medical image V formed by modality 105 may be temporarily stored in the database of the image storage server, and the three-dimensional medical image V may be transferred from the image storage server to image processing workstation 109 in response to a request from image processing workstation 109.

With respect to the hardware configurations, modality 1 in FIG. 1 and modality 105 in FIG. 13 may be an ultrasonic diagnostic system or a MRI system other than the CT system described above. Endoscope 101 in FIG. 13 may be a soft endoscope or a capsule endoscope, instead of the rigid endoscope. Further, for endoscope position detection unit 111 and treatment tool position detection unit 112, a magnetic encoder, or a gyro or rotary encoder as described in Japanese Unexamined Patent Publication No. 2005-021353 may be used.

Further, a region of a subject other than the liver or an abdominal cavity, such as a chest cavity or the like, may be the examination region.

In the processing performed by image processing workstation 3 and 109, three-dimensional medical image obtaining units 11 and 124 may be configure to obtain a three-dimensional image V before or during surgery. Here, in the case of the fifth embodiment, when a three-dimensional image V is obtained during surgery, the positions of endoscope 101 and treatment tool 106 may be detected from the three-dimensional image V obtained during the surgery by a known pattern recognition method without using endoscope marker 107a, treatment tool marker 107b, and position sensor 108. Further, where three-dimensional images are obtained continuously during surgery, it is preferable that an ultrasonic diagnostic system is used as modality 1 or 105 in order to reduce the amount of radiation received by the subject.

Lesion position identification unit 125 may be adapted to obtain information of lesion position $P_I$ associated as auxiliary information of the three-dimensional image V.

Intersection point detection units 16 and 127 may be adapted to parallel project the lesion position $P_I$ not to the surface position SF but to a position equivalent to the surface position SF, such as a position away from the surface position SF by several pixels.

Further, intersection point detection units 16 and 127 may be adapted to calculate the position of an intersection point $P_A$ between a straight line connecting the center of a lesion area $P_I$ and treatment tool position $P_T$ and indicating the operation direction and surface position SF, instead of parallel projecting the lesion position $P_I$ onto the surface position SF in the operation direction, while projection image generation unit 17 or virtual endoscopic image generation unit 128 is adapted to add an annotation, such as an arrow marker, a circle marker, a text comment, or the like, at the position of the intersection point $P_A$ in the projection image $I_P$ or the virtual endoscopic image $I_{VE}$.

Projection image generation unit 17 in the first embodiment may be adapted to generate a projection image $I_P$ by central projection. In this case, a processing unit for manually setting a viewpoint position is provided, instead of visual line setting unit 12.

An arrangement may be adopted in which the coordinate transformations performed in endoscope position obtaining unit 122 and treatment tool position obtaining unit 123 are performed in virtual endoscopic image generation unit 128.

What is claimed is:

1. A projection image generation apparatus, comprising:
   a projection image generation section for generating, using a three-dimensional medical image (V) as an input, a projection image (Ip) on a given projection plane of a display, the projection image being formed by projecting image information on a plurality of visual lines (VL) viewing a first structure in the three-dimensional medical image from a given viewpoint on the given projection plane;
   a treatment tool position setting section for setting an assumed position (Pt) of a treatment tool in a coordinate space of the three-dimensional medical image (V), the assumed position (Pt) i) corresponding to an actual position of the treatment tool in actual space, and ii) being distinct from the actual position of the treatment tool in actual space in that the assumed position (Pt) of the treatment tool is expressed in the coordinate space of the three-dimensional medical image (V) and the actual position of the treatment tool is expressed in actual space;
   a surface detection section for detecting a surface (SF) of the first structure from the three-dimensional medical image;
   a second structure identification section for identifying a second structure (Pi) in the three-dimensional medical image located at a position masked by the first structure (SF) when the first structure is viewed from the assumed position (Pt) of the treatment tool; and an intersection point detection section for detecting an intersection point (Pa) between an assumed movement path (TL1) formed when the treatment tool is moved from the assumed position (Pt) towards the second structure (Pi) and the surface of the first structure (SF), wherein, the projection image generation section generates the projection image (Ip) in which the intersection point (Pa) displayed in an identifiable manner at a position on the projection plane to which the image information on a corresponding visual line (VL1) connecting the given viewpoint and the intersection point is projected, the image information on the corresponding visual line (VL1) is a result obtained based on color information and cumulative capacity calculated by visual line direction ray casting and the image information indicates colors which are actually displayed on the display, wherein said ray casting i) determines whether a search point is on the surface (SF) of the first structure, ii) when the search point is determined to be on the surface (SF) of the first structure, the intersection point detection section calculates the color information (CTL) and the cumulative opacity ($\alpha$TL) by ray casting from the search point toward an inside of the subject in an operation direction TL, and then the projection image generation section performs visual line direction ray casting based on color information (CSF) allocated to the search point and the calculated color information (CTL) and the calculated cumulative opacity ($\alpha$TL), and iii) when the search point is determined not to be on the surface (SF) of the first structure, the projection image generation section performs visual line direction ray casting using the color information (CSF) allocated to the search point, the assumed movement path (TL1) and the corresponding visual line (VL1) connecting the given viewpoint and the intersection point (Pa) have different directions and intersect with each other at the intersection point (Pa).

2. The projection image generation apparatus of claim 1, wherein, the intersection point detection section detects the intersection point by projecting the second structure onto a portion of the surface of the first structure located in a direction from the second structure towards the assumed position of the treatment tool; and the projection image generation section displays the intersection point in an identifiable manner by projecting the second structure projected on the portion of the surface of the first structure onto the projection plane from the viewpoint.

3. The projection image generation apparatus of claim 2, wherein, the intersection point detection section further projects a third structure located in front of the second structure when the second structure is viewed from a position of the treatment tool onto a portion of the surface of the first structure located in a direction from the second structure towards the assumed position of the treatment tool.

4. The projection image generation apparatus of claim 2, wherein the projection from the given viewpoint onto a portion of the surface of the first structure is a parallel projection of the visual lines.

5. The projection image generation apparatus of claim 1, wherein, the apparatus further comprises an endoscope position detection section that detects a position of an endoscope inserted into a body cavity of a subject in real time; and the given viewpoint position is a position in the coordinate space of the three-dimensional medical image corresponding to the position of the endoscope detected by the endoscope position detection section.

6. The projection image generation apparatus of claim 5, further comprising:

a real endoscopic image forming section that forms a real endoscopic image representing an inside of the body cavity by real time imaging; and a superimposed image generation section that generates a superimposed image in which the real endoscopic image and a further projection image based on the position of the endoscope detected by the endoscope position detection section at substantially the same timing as that of the formation of the real endoscopic image are superimposed.

7. The projection image generation apparatus of claim 1, wherein, the apparatus further comprises a treatment tool position detection section that detects a position of a treatment tool inserted into a body cavity of a subject in real time; and the assumed position of the treatment tool is a position in the coordinate space of the three-dimensional medical image corresponding to the position of the treatment tool detected by the treatment tool position detection section.

8. The projection image generation apparatus of claim 1, wherein the second structure is a target region for surgery.

9. The projection image generation apparatus of claim 3, wherein the third structure is an anatomical structure that requires attention during surgery, the third structure being at least one of a blood vessel, an internal organ, and a tumor located on a vicinity of the assumed movement path of the treatment tool moving towards the second structure.

10. A projection image generation method, comprising the steps of:

generating, using a three-dimensional medical image as an input, a projection image (Ip) on a given projection plane of a display, the projection image formed by projecting image information on a plurality of visual lines viewing a first structure in the three-dimensional medical image from a given viewpoint on the given projection plane;

setting an assumed position (Pt) of a treatment tool at a position on a front and outside of the first structure when the first structure is viewed from the viewpoint in a coordinate space of the three-dimensional medical image, the assumed position (Pt) i) corresponding to an actual position of the treatment tool in actual space, and ii) being distinct from the actual position of the treatment tool in actual space in that the assumed position (Pt) of the treatment tool is expressed in the coordinate space of the three-dimensional medical image (V) and the actual position of the treatment tool is expressed in actual space;

detecting a surface of the first structure from the three-dimensional medical image;

identifying a second structure in the three-dimensional medical image located at a position masked by the first structure when the first structure is viewed from the assumed position of the treatment tool; and detecting an intersection point between an assumed movement path formed when the treatment tool is moved from the assumed position towards the second structure and the surface of the first structure, wherein, the step of generating a projection image generates the projection image in which the intersection point is displayed in an identifiable manner at a position on the projection plane to which image information on a corresponding visual line connecting the viewpoint and the intersection point is projected, the image information on the corresponding visual line (VL1) is a result obtained based on color information and cumulative capacity calculated by visual line direction ray casting and the image information indicates colors which are actually displayed on the display, wherein said ray casting i) determines whether a search point is on the surface (SF) of the first structure, ii) when the search point is determined to be on the surface (SF) of the first structure, calculates the color information (CTL) and the cumulative opacity (αTL) by ray casting from the search point toward an inside of the subject in an operation direction TL, and then performs visual line direction ray casting based on based on color information (CSF) allocated to the search point and the calculated color information (CTL) and the calculated cumulative opacity (αTL), and iii) when the search point is determined not to be on the surface (SF) of the first structure, performs visual line direction ray casting using the color information (CSF) allocated to the search point, the assumed movement path (TL1) and the corresponding visual line (VL1) connecting the given viewpoint and the intersection point (Pa) have different directions and intersect with each other at the intersection point (Pa).

11. A non-transitory computer readable medium on which is recorded a projection image generation program for causing a computer to perform the steps of:

generating, using a three-dimensional medical image as an input, a projection image (Ip) on a given projection plane of a display, the projection image formed by projecting image information on a plurality of visual lines viewing a first structure in the three-dimensional medical image from a given viewpoint on the given projection plane;

setting an assumed position of a treatment tool in a coordinate space of the three-dimensional medical image, the assumed position (Pt) i) corresponding to an actual position of the treatment tool in actual space, and ii) being distinct from the actual position of the treatment tool in actual space in that the assumed position (Pt) of the treatment tool is expressed in the coordinate space of the three-dimensional medical image (V) and the actual position of the treatment tool is expressed in actual space;

detecting a surface of the first structure from the three-dimensional medical image;

identifying a second structure in the three-dimensional medical image located at a position masked by the first structure when the first structure is viewed from the assumed position of the treatment tool; and detecting an intersection point between an assumed movement path formed when the treatment tool is moved from the assumed position towards the second structure and the surface of the first structure, wherein, the step of generating a projection image generates the projection image in which the intersection point is displayed in an identifiable manner at a position on the projection plane to which image information on a corresponding visual line connecting the viewpoint and the intersection point is projected, the image information on the corresponding visual line (VL1) is a result obtained based on color information and cumulative capacity calculated by visual line direction ray casting and the image information indicates colors which are actually displayed on the display, wherein said ray casting i) determines whether a search point is on the surface (SF) of the first structure, ii) when the search point is determined to be on the surface (SF) of the first structure, calculates the color information (CTL) and the cumulative opacity (αTL) by ray casting from the search point toward an inside of the subject in an operation direction TL, and then performs visual line direction ray casting based on based on color information (CSF) allocated to the search point and the calculated color information (CTL) and the calculated cumulative opacity (αTL), and iii) when the search point is determined not to be on the surface (SF) of the first structure, performs visual line direction ray casting using the color information (CSF) allocated to the search point, the assumed movement path (TL1) and the corresponding visual line (VL1) connecting the given viewpoint and the intersection point (Pa) have different directions and intersect with each other at the intersection point (Pa).

12. The projection image generation apparatus of claim 1, wherein,
the first structure is an organ, and
the second structure is a lesion present inside of the organ.

13. The projection image generation apparatus of claim 1, wherein,
the first structure is a body surface, and
the second structure is treatment target within the body and below the body surface.

14. The method of claim 10, wherein,
the first structure is an organ, and
the second structure is a lesion present inside of the organ.

15. The method of claim 10, wherein,
the first structure is a body surface, and
the second structure is treatment target within the body and below the body surface.

16. The non-transitory computer readable medium of claim 11, wherein,
the first structure is an organ, and
the second structure is a lesion present inside of the organ.

17. The non-transitory computer readable medium of claim 11, wherein,
the first structure is a body surface, and
the second structure is treatment target within the body and below the body surface.

18. The projection image generation apparatus of claim 1, wherein,
the first structure is defined by a body surface,
the second structure is treatment target within the body and below the body surface,
the given viewpoint is a visual viewpoint, in the coordinate space of the three-dimensional medical image, corresponding to an operator operating an endoscope in actual space,
the corresponding visual line (VL1) extends from the visual viewpoint of the operator and from the endoscope towards the body surface defining the first structure, and
the assumed movement path (TL1) of the treatment tool is an operation direction of the treatment tool towards the treatment target and passing through the body surface.

19. The method of claim 10, wherein,
the first structure is defined by a body surface,
the second structure is treatment target within the body and below the body surface, the given viewpoint is a visual viewpoint, in the coordinate space of the three-dimensional medical image, corresponding to an operator operating an endoscope in actual space, the corresponding visual line (VL1) extends from the visual viewpoint of the operator and from the endoscope towards the body surface defining the first structure, and the assumed movement path (TL1) of the treatment tool is an operation direction of the treatment tool towards the treatment target and passing through the body surface.

20. The non-transitory computer readable medium of claim 11, wherein, the first structure is defined by a body surface, the second structure is treatment target within the body and below the body surface, the given viewpoint is a visual viewpoint, in the coordinate space of the three-dimensional medical image, corresponding to an operator operating an endoscope in actual space, the corresponding visual line (VL1) extends from the visual viewpoint of the operator and from the endoscope towards the body surface defining the first structure, and the assumed movement path (TL1) of the treatment tool is an operation direction of the treatment tool towards the treatment target and passing through the body surface.

* * * * *